United States Patent [19]

Arima et al.

[11] Patent Number: 5,481,917
[45] Date of Patent: Jan. 9, 1996

[54] ULTRASONIC INSPECTION AND IMAGING INSTRUMENT

[75] Inventors: Yukio Arima, Thukuba; Toshihiro Kimura, Ibaraki; Tohru Miyata; Yuichi Kunitomo, both of Tsuchiura, all of Japan

[73] Assignee: Hitachi Construction Machinery Co., Ltd., Tokyo, Japan

[21] Appl. No.: 290,960

[22] PCT Filed: Jan. 5, 1994

[86] PCT No.: PCT/JP94/00003

§ 371 Date: Aug. 24, 1994

§ 102(e) Date: Aug. 24, 1994

[87] PCT Pub. No.: WO94/16321

PCT Pub. Date: Jul. 21, 1994

[30] Foreign Application Priority Data

Jan. 6, 1993 [JP] Japan .................................. 5-016760

[51] Int. Cl.$^6$ .................................................. G01N 29/04
[52] U.S. Cl. .................................................. 73/621; 73/618
[58] Field of Search .............................. 73/618, 619, 621, 73/625

[56] References Cited

U.S. PATENT DOCUMENTS

| | | | |
|---|---|---|---|
| 4,649,927 | 3/1987 | Fehr et al. | 73/625 |
| 4,747,411 | 5/1988 | Ledley | 73/621 |
| 5,062,429 | 11/1991 | Smith et al. | 73/625 |
| 5,088,496 | 2/1992 | Bernard | 73/625 |
| 5,179,954 | 1/1993 | Arima et al. | 73/621 |
| 5,249,577 | 10/1993 | Shinomura et al. | 73/625 |

FOREIGN PATENT DOCUMENTS

| | | |
|---|---|---|
| 63-83664 | 4/1988 | Japan . |
| 3-73846 | 3/1991 | Japan . |
| 4-62467 | 2/1992 | Japan . |

*Primary Examiner*—Richard Chilcot
*Assistant Examiner*—Max Noori
*Attorney, Agent, or Firm*—Fay, Sharpe, Beall, Fagan, Minnich & McKee

[57] ABSTRACT

A scanning range of an object under examination is divided into m pieces (m is an integer equal to or more than 2) in a subscanning direction. One measurement condition or one parameter is set in m steps, and an ultrasonic measurement is performed on the object under examination while allotting successively the m-stepped measurement conditions or the m-stepped parameters to the respective scanning regions divided in the subscanning direction. A plurality of measurement images obtained under the m-stepped measurement conditions are displayed so as to permit comparison on a screen, and one of the m-stepped measurement conditions or m-stepped parameters which corresponds to an image selected from the displayed screen is set as the measurement condition.

10 Claims, 5 Drawing Sheets

ULTRASONIC INSPECTION AND IMAGING INSTRUMENT

TECHNICAL FIELD

The present invention relates to an ultrasonic inspection and imaging instrument and more particularly relates to an ultrasonic inspection and imaging instrument which permits any person who is inexperienced in ultrasonic measurement to readily select an optimum or a proper measurement condition.

BACKGROUND TECHNOLOGY

An urtrasonic inspection and imaging instrument as one of ultrasonic measurement instruments is capable of displaying the interior of an object under examination in the form of a B- and a C- scope image. An imaging instrument of this sort, in order to obtain a clear image, necessitates such as setting and selection of various measurement conditions including acoustic characteristic of its probe, sound velocity in a medium and an object under examination at their instant temperature and the like, setting a gate in the object under examination at a desired depth according to the selected measurement condition and further, focusing operation setting the focus for the probe.

Conventionally, for the gate setting and the focusing operation, a reflection waveform (an A scope image) from the object under examination was observed by using an oscilloscope or the like, a desired measurement depth, detection gate width and the like were set according to the observed waveform as well as an operation of moving up and down (positioning in Z direction) of a focusing type ultrasonic probe (hereinafter simply called as probe) with respect to the object under examination was performed so as to focus the probe at a desired measurement depth and further to maximize a target reflection echo.

However, in case of an inspection of defects existing inside a measurement specimen such as cracks, voids and foreign matters, the shapes of the defects are indefinite, for this reason the intensities of defect echos from these defects vary and could not be detected in a uniform manner. Further, the location and depth of defects are frequently indeterminable in certain types of objects under examination. For this reason, a measurement is performed by provisionally selecting setting values and setting measurement conditions.

Accordingly, for the purpose of selecting an optimum measurement condition for a certain object under examination, such as proble height, probe gain and gate position which provide an optimum image are determined while observing images obtained by probe scanning. In particular, in an arrangement in which such as the probe height, probe gain and gate position are set via a computer control there are many setting numbers for the measurement conditions or for their parameters and the programs are started on every condition and setting such that it takes great many time for the operation. Moreover, there is no guarantee that the measurement condition with regard to the above items is an optimum one which is resulted from the several time measurements.

This is because that such as the probe gain, gate position, focusing position and defect condition are affected each other and even when one of the parameters is modified while monitoring an image under a certain measurement condition the condition of the other parameters vary such that a desired measurement image can not be frequently obtained unless all of the parameters are reset. In such instance one particular parameter is noted and only the value of the noted parameter is varied so as to select a measurement condition while fixing the values of the other parameters, however since there are so many parameters that it takes long time for selecting an optimum measurement condition. Moreover, when the noting is changed[ to another parameter and the relationship between the previously noted parameter of which value are already determined and the presently noted parameter is at the same time varied, the setting operations are frequently messed up.

Because of the above circumstances, a setting of an optimum measurement condition for a measurement specimen is comparatively difficult and time comsuming except for an experienced person and an expert who have experiences in the ultrasonic measurement and well know the relation between measurement images and corresponding defects.

An object of the present invention is to resolve such conventional problems and to provide an ultrasonic inspection and imaging instrumrnt which permits even for a person inexperienced in an ultrasonic measurement to easily set an optimum or close to optimum proper measurement condition.

DISCLOSURE OF THE INVENTION

For achieving such object, in the constitution of an ultrasonic inspection and imaging instrument according to the present invention, a scanning range of an object under examination is divided into m pieses (m is an integer equal to or more than 2) in a subscanning direction, one of measurement conditions or one of its parameters is set in m steps, an ultrasonic measurement is performed on the object under examination while allotting successively the m stepped measurement conditions or the m stepped its parameters to the respective scanning regions divided in the subscanning direction, a plurality of measurement images obtained under the m stepped measurement conditions are displayed so as to permit comparison on a screen, and one of m stepped measurement conditions or m stepped its parameters which corresponds to an image selected from the displayed screen is set as the measurement condition.

Further, in one modification of the present invention, the m stepped scanning is set for a same XY plane scanning range and every time when the m stepped measurement conditions are renewed scanning over the same range is repeated to perform m time measurements. By doing so m pieces of images over the same portion under m sorts of different measurement conditions can be sampled and a plurality of measurement images obtained are successively displayed so as to permit comparison on the screen.

Further, the present invention includes means for correlating one of m stepped measurement conditions with a corresponding display image through the selection of one of m stepped measurement images each corresponding to one of m stepped measurement conditions.

Accordingly, through dividing the scanning range into m pieces in the subscanning direction and performing measurement while setting one of measurement conditions for respective scanning regions of m steps, the measurement images displayed on a screen as one picture are a series of images corresponding to m sorts of measurement conditions. Therefore through observation and comparison of the images under different measurement conditions and displayed successively and selecting one proper image, an optimum or a proper measurement condition among m sorts of measurement conditions can be easily set.

For example, when a measurement is performed by making use of a certain measurement condition roughly divided into m steps, a proper measurement condition can be estimated by the first measurement. Subsequently, when another measurement is performed by making use of the estimated proper measurement condition finely divided into q steps, a setting value of an optimum or close to optimum proper measurement condition can be easily obtained by this second measurement. When the above operation is performed respectively for a plurality of measurement parameters, respective optimum or close to optimum proper measurement conditions can by easily selected for many measurement conditions. Further, with regard to mutually affecting measurement conditions, after determining one measurement condition a measurement is again performed by dividing again the previously determined measurement condition into m pieces, thereby an optimum condition can be easily selected.

PREFERRED EMBODIMENTS FOR REDUCING INTO PRACTICE THE INVENTION

Figure 1:
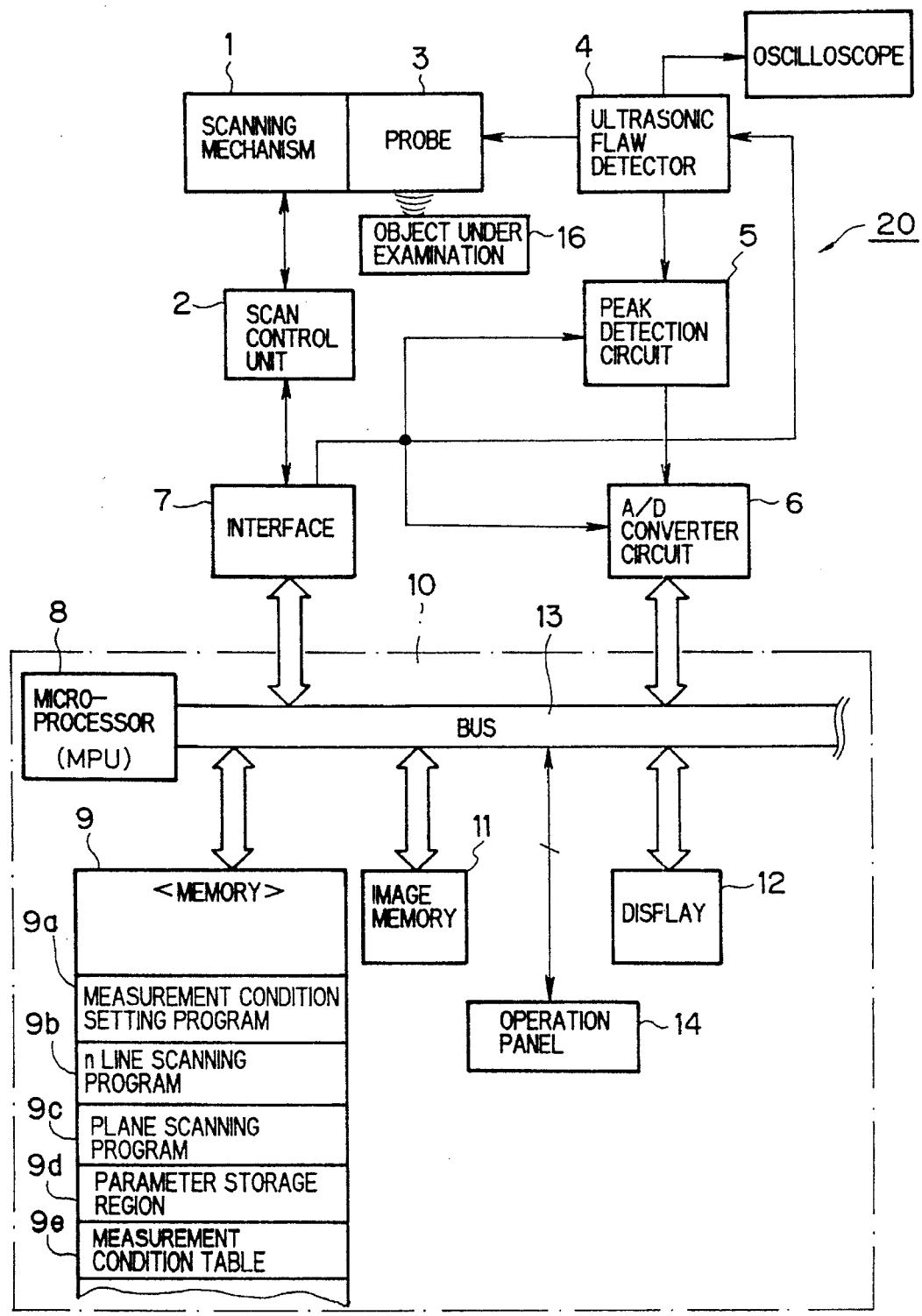
FIG. 1 is a block diagram of one embodiment of ultrasonic inspection and imaging instruments according to the present invention.

In FIG. 1, numeral 20 is an ultrasonic inspection and imaging instrument wherein 1 is a scanning mechanism therefor having a XYZ direction moving mechanism. A focusing type probe 3 is mounted on the scanning mechanism 1 and performs a main scanning in X direction and a subscanning in Y direction over an object under examination 16. The ultrasonic inspection and imaging instrument 20 obtains A scope images of respective measurement points via the XY scanning, produces based on the A scope images measurement data of B scope images and measurement data of C scope images and includes a function of displaying the B scope images and C scope images. Further, there exists inside the object under examination 16 material defects such as voids, foreign matters and cracks.

The scanning mechanism 1 is controlled by a scann control unit 2 and the scann control unit 2 is controlled by a system control unit 10 via an interface 7.

The probe 3 is connected to an ultrasonic flaw detector 4 and the ultrasonic flaw detector 4 is constituted by a pulser-receiver and the like, sends a pulse signal at a predetermined measurement period to the probe 3 from its signal transmission terminal in response to the control signal from the system control unit 10, receives at its signal receiving terminal an echo receiving signal from the probe 3 obtained in response to the generation of the pulse signal and amplifies the same and further after detecting the same sends out to a peak detection circuit 5.

The peak detection circuit 5 sets a gate at a predetermined position on the detected echo receiving signal and detects a necessary peak value in the echo receiving signal component. The detected peak value is outputted to an A/D converter circuit 6. The gate position is determined by a setting signal from the system control unit 10 via the interface 7. In addition to the peak value detection the peak value detection circuit 5, for example, detects a surface echo and performs a time counting in response to the setting signal. Therefore a circuit for this purpose is incorporated in the peak detection circuit.

The A/D converter circuit 6 converts the obtained peak value of analog signal into, for example, digital signal of 8 bits in 256 steps in response to a control signal from the system control unit 10 and sends out to a bus 13 in a form of an input data value which permits processing by a microprocessor (MPU) 8 in the system control unit 10. Further, if required the time count value data is also sent out to the MPU 8.

As a result, measurement values at respective measurement points when the probe 3 scans over the object under examination in X direction are detected via the peak detection circuit 5 and are transferred to the MPU 8. The MPU 8 successively stores these peak value data into memory 8 while correlating to the respective measurement points.

In addition to the MPU 8, an operation panel 14, the memory 9 storing a variety of programs and data, an image memory 11, a display 12 and the like are connected to the bus 13. Further, the display 12 incorporates in its inside a video memory, video controller and the like.

The memory 9 stores such as a step like measurement condition setting program 9a, an n line scanning program 9b, a plane scanning program 9c and a display processing program. Further, a parameter storage region 9d and a measurement condition table 9e are provided in the memory 9 and in the parameter storage region 9d, for example, number of times n of subscanning, probe height h, scanning width (Wx, Wy), coordinate of scan starting point (Xo, Yo), gate position to, gate width Wo, receiver gain Go, applied voltage Vo on the probe from the pulser, measurement pitch Po, pulse creating interval Lo from the pulser, trigger level To of the pulser and threshold level THo for judging whether or not a measurement data is defective, are stored. These parameters are either set beforehand via the opeartion panel 14 or set as initial values, and are rewritten via the step like measurement condition setting program 9a depending on the measurement conditions.

The step like measurement condition setting program 9a is executed when a fuction key for n division measurement is inputted from the operation panel 14, determines the subscanning line number n obtained by dividing a horizontal scanning line number, for example 400 lines, which is allotted for a display area of measurement images of one screen picture with the inputted step number m (wherein m is an integer, n is an integer portion of the quotient and the decimals thereof are omitted) and stores the value as the subscanning number n in the parameter storage region 9d, and further generates m pieces of parameters m1, m2, m3, ... mm in m steps within a designated range of the parameter designated via the operation panel 14 by making use of the step number m and stores these parameters in the measurement condition table 9e. For example, an applied voltage can be selected as a measurement condition which is set in stepwise and since the range thereof is from 50 V to 250 V, when it is desired to perform a measurement while varying the range in 5 steps, m=5 and n=400/5=80. Accordingly, the m stepped parameters of the applied voltage are 50 V, 100 V, 150 V, 200 V and 250 V which are successively stored in the measurement condition table 9e.

The step like measurement condition setting program 9a is executed in response to an input of the measurement start key for executing the n divided measurement.

Further, the step like measurement condition setting program 9a is started by the n line scanning program 9b every time when scanning of n lines according to the n line scanning program 9b is completed. When starting a measurement, parameters in the parameter storage region 9d which have to be set for certain circuits as the measurement condition are set for respective circuits requiring setting of such parameters as well as after either setting parameters for circuits necessitating such parameters as the measurement condition with reference to the parameter on the first line in the measurement condition table 9e or rewriting the corresponding parameters in the parameter storage region 9d by parameters on the first line in the measurement condition table 9e, the n line scanning program 9b is started. Further every time when scanning of n lines is completed, in other words, every time when scanning of each of the n divided scanning regions in the subscanning direction is completed, the parameter subsequent to the previously referred to parameter in the measurement condition table 9e is referred to, then the previous parameter is rewritted by the subsequent parameter and after setting a measurement condition the n line scanning program 9b is started. Such starting is repeated until the m stepped measurements are completed. Further, the parameters set in step wise are separated from the others such as by flagging in the parameter storage regions 9d.

Now, there are two types of scanning methods for the n line scanning program 9b. The selection of one among the two methods are performed by selecting initial conditions.

In the first method, a predetermined scanning range on the XY plane is divided into m regions in subscanning direction and is scanned, and m pieces of images taken under respectively different measurement conditions are successively displayed on a screen so as to permit comparison therebetween. In this case, even after completing scanning by n lines in subscanning direction it is unnecessary to change the position of the probe, in that the probe is just positioned at the starting position for the subsequent horizontal scanning which is identical with the ordinary plane scanning.

In the second method, the m stepped scannings are set for the common XY plane scanning range, in that the common XY scanning range is repeatedly scanned while successively renewing the measurement conditions in m steps to perform measurement in m times. In this case, after completing scanning by n lines in scanning direction the probe position returns to the original position in the first scanning range. Namely, every time when once the execution of the n line scanning program 9b has been completed, the probe returns to the original position (Xo, Yo) in the XY scanning range (scanning width (Wx, Wy)), scanning over the same XY range is again performed and these scannings are repeated m times to complete the scanning for the n divided measurement. The obtained measurement data are processed to be displayed on a subsequent display region extending by n lines from a horizontal scanning line so as to permit comparison between displayed images on a screen and a plurality of the measurement images of respective measurement conditions are successively displayed on the screen.

In either scanning methods, for the example, of 5 stepped measurement conditions, the scanning line number 80 is stored in the parameter storage region 9d via the step like measurement condition setting program 9a. Parameters 50 V, 100 V, 150 V, 200 V and 250 V are stored in this order in the measurement condition table 9e as parameters for the applied voltage. When the n line scanning program 9b performs a horizontal scanning by 80 lines with reference to the scanning line number 80 in the parameter storage region 9d, the scanning operation is once terminated.

Accordingly, for example when a measurement is performed while varying the applied voltage in 5 steps, in that from 50 V to 250 V, for the first line to 80th line of the main scanning a XY scanning is performed while keeping the voltage (applied voltage) of the transmission signal pulse at 50 V and the measurement data therefrom are sampled out, for the 81th line to 160th line the measurement data are sampled out at the applied voltage 100 V, for the 161th line to 240th line the measurement data are sampled out at the applied voltage 150 V, subsequently, in response to alternation of the covering scanning lines by 80 lines the applied voltage is successively set at 200 V and 250 V and measurements are performed.

Further, for example, when a certain line in a measurement image displayed on a screen is designated by a cursor and an input is effected via the operation panel 14 based on the designation, the step like measurement condition setting program 9a selects a parameter for the scanning region corresponding to the designated line from the measurement condition table 9e and writes the same as a selected parameter at the position of the corresponding parameter in the parameter storage region 9d. In this instance, when the respective measurement conditions (parameter values) are designed to be displayed on the screen in association with the measurement images which correspond to the respective scanning regions, the parameter value corresponding to the image to be selected can be input directly via the operation panel 14 without relying on the cursor designation.

In the above example, when the image from 161th line to 240th line is selected, in the region in the parameter storage region 9d where the parameters for the applied voltage are stored a parameter representing a voltage of 150 V is written in. As a result, when afterward the function key for the n divided measurement is again inputted for performing an n divided measurement using another parameter, the step like measurement condition setting program 9a sets the parameter of applied voltage of 150 V stored in the parameter storage region 9d on the pulser as an effective set value.

The n line scanning program 9b performs an ultrasonic measurement by the amount of n lines for the subscanning with reference to respective parameters stored in the parameter storage region 9d and according to the value of the scanning line number n likely stored therein, after completing the measurement, performs processings to produce display data from the measurement data of the amount corresponding to the main scanning line number n and to display the measurement image at the position on a screen corresponding to the scanning area. In this instance, it is needless to say that every time when a measurement data is received in response to main scanning of one line the display data can be produced and displayed. In the present example, for the sake of convenience, it is assumed that one line for the main scanning lines corresponds to one line for the horizontal scanning lines and one line of the subscanning lines to one line of Y direction scanning lines. However, Y direction can be assumed as main scanning direction and X direction as subscanning direction. Further, it is also needless to say that when scanning in Z direction is selected for the purpose of such as for setting the probe height and the foucusing operation, the Z direction can be treated as a main scanning direction or a subscanning direction.

Further, when the n line scanning program 9b is executed, the MPU 8 sets the probe 3 at an original point in the designated XY scanning range, starts a horizontal scanning and receives measurement data of 256 gradations which are determined by A/D conversion of the peak values detected at respective measurement positions along the horizontal scanning. Further, in case that the display data are produced every time when the measurement data are received, the measurement data of 256 gradations are developed into display data corresponding to scanning positions in XY plane and are successively stored in respective memory positions in the image memory 11 corresponding to the display positions. The data stored in the image memory 11 are transferred to the display 12 via the display processing program and are displayed. When scanning of one line for horizontal scanning is completed, the scanning line is moved by an amount of one pitch for subscanning, then the same scanning operation is repeated until subscanning amounting to n time scannings is completed, and the display data amounting to the n time subscannings are successively stored in the image memory 11 and at the same time successively displayed.

Figure 2:
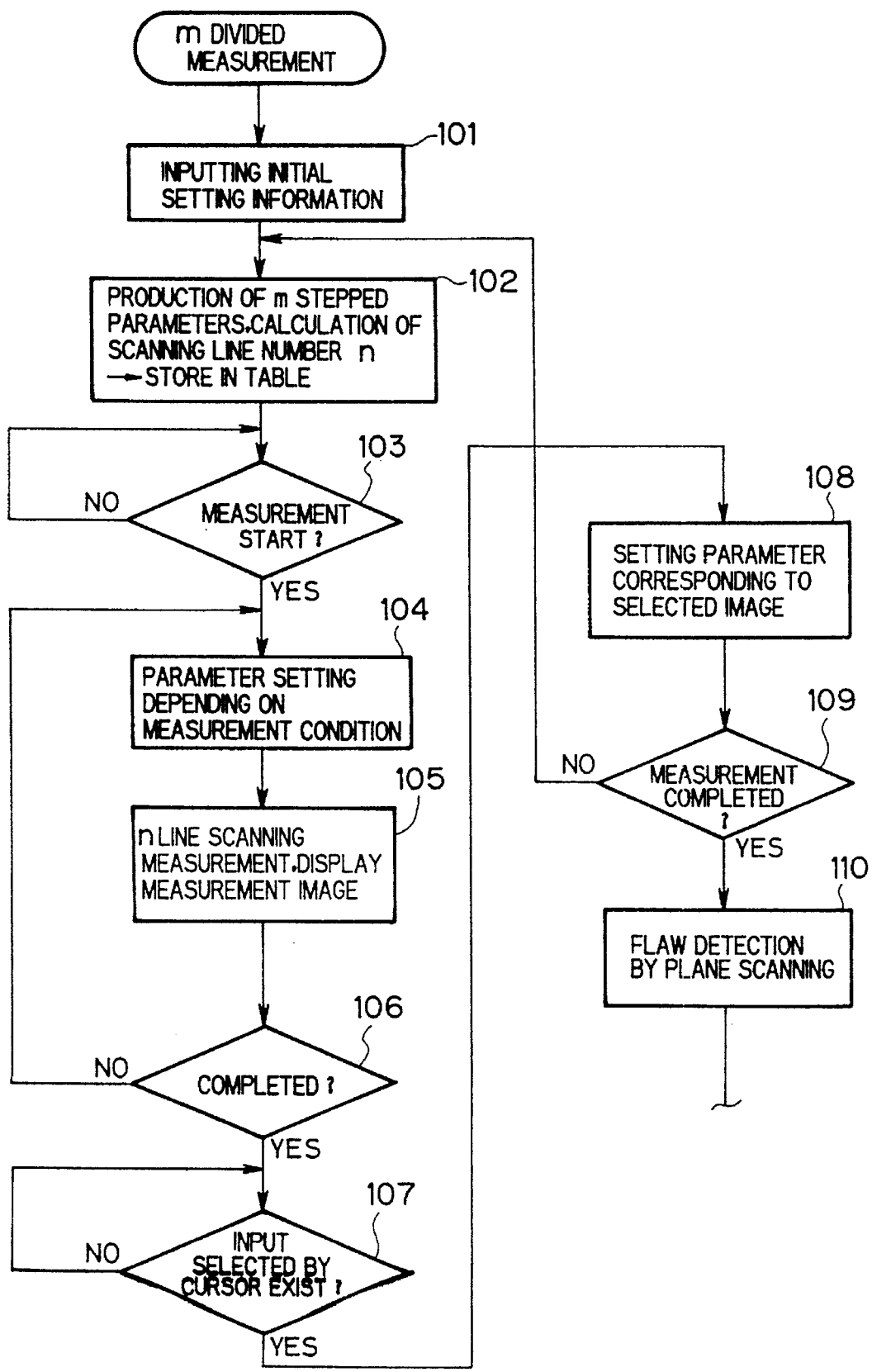
FIG. 2 is a flowchart of a m divided measurement processing.

Now, the overview operation of the present embodiment is explained with reference to the flowchart as shown in FIG. 2.

At first, in step 101 a group of measurement parameters are stored in the parameter storage region 9d based on the inital setting conditions inputted from the operation panel 14. Then in step 102, in response to inputting of the function key for the n divided measurement the step like measurement condition setting program 9a is started m stepped parameters corresponding to the inputted steep number with regard to the designated parameter are produced and stored in the measurement condition table 9e, and further the scanning line number n is calculated and stored in the parameter storage region 9d.

Figure 3:
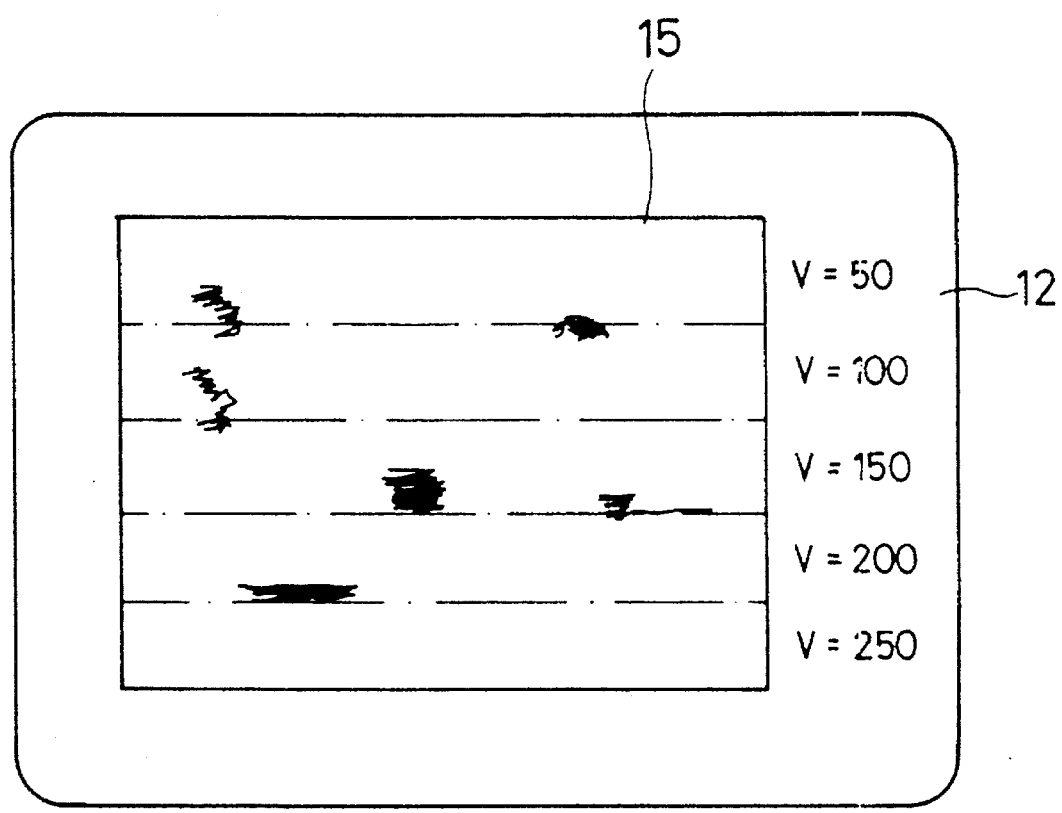
FIG. 3 is a view for explaining the measurement images through the processing.

In the subsequent step 103, the process enters into a waiting loop for judging whether the measurement is started. When the function key for the measurement start is inputted via the operation panel 14, the step like measurement condition setting program 9a is executed in step 104, the initial measurement conditions are set for the respective circuits and the parameters in the parameter storage region 9d are rewritten and reset accoding to the measurement conditions stored in the measurement condition table 9e. Then in step 105 the n line scanning program 9b is started to perform the n line scanning and the measurement images are displayed. In step 106, it is judged whether the scanning operation is completed, if the scanning operation amounting m stepped measurements is not completed, the process returns to step 104 where in the measurement conditions in the parameter storage region 9d are rewritten by the subsequent measurement conditions stored in the measurement condition table 9e, then in step 105 the subscanning amounting to n lines of the subsequent main scanning is performed and the measurement wherein the measurement condition varies in step wise by every n line scanning is repeated. As a result, the measurement images as illustrated in FIG.3 are, for example, obtained. In FIG. 3, numeral 15 is a display area for the measurement images and the lines indicated by one-dot chain line correspond to boundaries of m divided scanning regions and are imaginary lines for illustrating m step division of the display area on the screen.

After completion of the scanning, in step 107 the process enters into a judging step whether the input is via designation of images on the screen by the cursor, and when it is judged that a specific image is selected by the cursor, the parameter for the measurement condition corresponding to the display line of the selected image is read out from the measurement condition table 9e in step 108 and are written in the parameter storage region 9d. In step 109, it is judged whether the measurement has been completed, if the measurement is not completed, the process returns to step 102 wherein the function key for the n divided measurement is inputted and another parameter for the subsequent setting is designated. For the designated other parameter the similar step wise condition setting is likely performed and a parameter for an optimum measurement condition is searched for based on the measurement images. Thereafter, in step 110 the plane scanning program 9c is started for example and a flaw detection of the object under examination is performed via the plane scanning according to the optimum or proper measurement condition set in the previous step.

With regard to correspondence between the respective designated n divided images on the display screen and the respective parameters on the measurement condition table 9e, since the arrangement order of the images is matched with that of the measurement parameters, it is enough to simply specify the allotted order.

Namely, the order of a designated image on the display screen can be calculated in the following manner, in that the vertical address (1~400) of the cursor is obtained from the display 12, then the address number is divided by n for the n line scanning and finally 1 is added to the integer part of the quotient to determined the order.

With regard to the 5 stepped display in the previous example, since n=80, when assuming the vertical address of the cursor is 170 then the quotient 170/80=2,125. Therefore the order is 2+1=3. Accordingly, the third parameter stored in the measurement condition table 9e is selected. These procedures are identical when the image is selected via a mouse, touch screen and the like.

Other than the above, when reference numerals or measurement parameters are displayed for the respective corresponding divided images, a measurement condition to be selected can be set by directly inputting a determined reference numeral or measurement parameter via the operation panel 14.

Through the above explained processings, a plurality of measurements determined by the step number can be performed once, moreover images of different measurement conditions are successively displayed, accordingly the relation between difference of the measurement condition and the measurement images is easily grasped. Further, in the present procedure after determining another parameter the previous parameter can be reselected via second time step setting, therefore a proper measurement condition can be easily selected and no significant time is required for the measurement condition setting.

In the present embodiment, an example of the applied voltage is specifically mentioned as the selectable parameter, however parameters which can be selected as a measurement condition set in step wise include all of the parameters stored in the parameter storage region 9d such as number of times n of subscanning, probe height h, scanning width (Wx, Wy), coordinate of scan starting point (Xo, Yo), gate position to, gate width Wo, receiver gain Go, applied voltage Vo on the probe from the pulser, measurement pitch Po, pulse creating interval Lo from the pulser, trigger level To of the pulser and threshold level THo for judging whether or not a measurement data is defective, are stored, and the manner of the step wise division is not limited to the uniform division as in the case of the applied voltage.

Now, a specific example wherein assuming that a plurality of measurement conditions is m=5 and a successive scanning over the XY scanning region is performed via 5 stepped divided measurement is explained with reference to FIG. 4 through FIG. 8.

Figure 4:
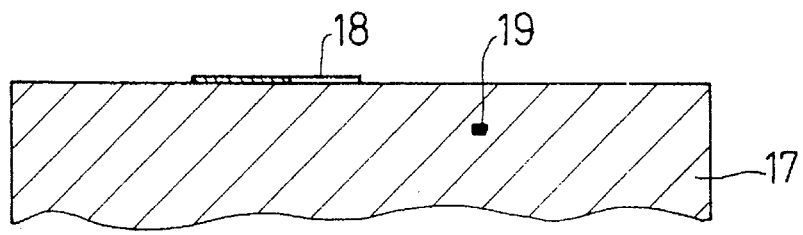
FIG. 4(a) is a cross sectional view of an object under examination constituting a measurement object taken along the line I—I in FIG. 4(b)
FIG. 4(b) is a plane view of FIG. 4(a)
Figure 4:
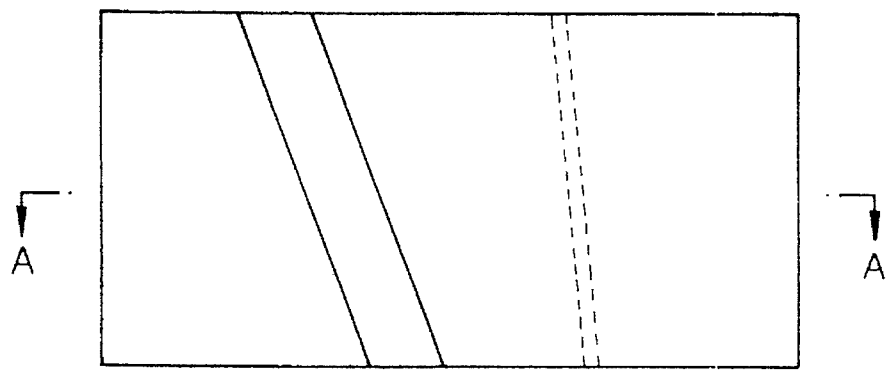

In the present example, an object for the measurement is the object under examination 17 as illustrated in FIG. 4. On the surface of the object a plating layer having a predetermined width is provided, and inside the object a metal wire 19 having rectangular cross section is embedded.

For the first time, in step 101 in FIG. 2, the probe 3 of a focusing type probe is positioned by inputting a probe height via the operation panel 14 so that the focal point of the probe comes onto the surface position of the object under examination 17 depending on the focal distance. Then, the XY scanning range is set so as to cover the range including the object under examination 17 and to permit the m stepped successive measurement. For the gate width, gate position, receiver gain, applied voltage and other setting conditions, standard measurement conditions therefor are provided as their initial conditions.

In the subsequent step 102, the function key for the m divided measurement is input, a probe position as a parameter is selected and the range of the position is set at 5 mm with a pitch of −1 mm. Then the division number m=5 is inputted. The minus symbol of the pitch for the probe height implies to move the probe 3 close to the side of the object under examination 17, in other words the height is gradually lowered.

Figure 5:
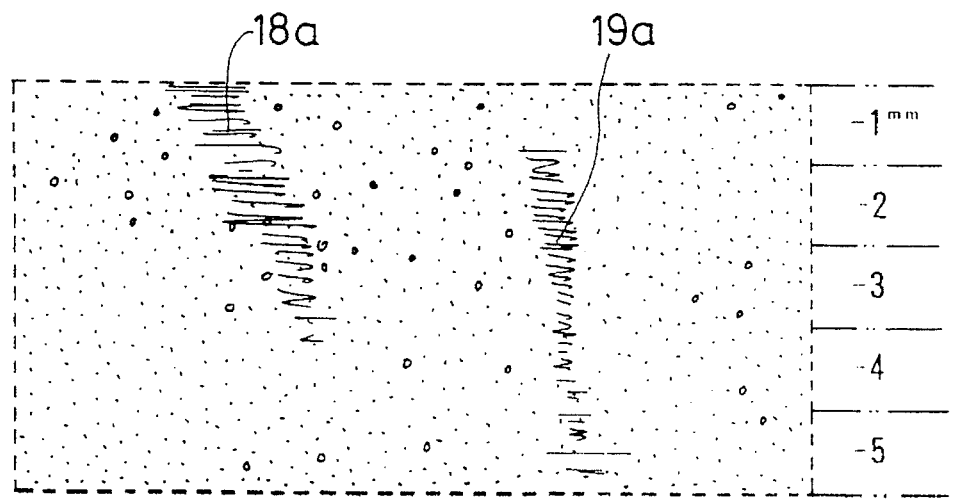
FIG. 5 is a view for explaining measurement images obtained when the probe height position is set in 5 steps with respect to the object under examination shown in FIG. 4.

When the measurement start key is inputted in step 103 and thereafter when the process is completed in step 106, the images as illustrated in FIG. 5 are obtained.

In the first image of the probe height at −1 mm, since an echo of the plating layer 18 on the surface is large, an image 18a corresponding to the plating layer appears, in the subsequent image of the probe height at −2 mm the plating layer image 18a becomes thin, in the image of the probe height at −3 mm plating layer image 18a becomes further thinner and the plating layer image 18a is disappeared from the images of probe heights at −4 mm~−5 mm. Contrary thereto, a thin image 19a of the wire material 19 appears in the image of the probe height at −2 mm, a clear wire metal image 19a appears in the image of the probe height at −3 mm, but the wire metal images 19a become gradually thin in the images of the probe height at −4 mm~5 mm.

According to the above measurement images, when it is desired to detect defects possibly existing along a horizontal plane near the layer of the wire material 19, the position at −3 mm for the height of the probe 3 can be selected.

An operator can input the selected position through the operation panel 14 either by moving the cursor onto the image corresponding to the probe height at −3 mm or by directly inputting the numeral value of −3 mm.

With the above operation the third display image is designated, the third parameter −3 mm stored in the measurement condition table 9e is selected in step 108 and a parameter which sets the height of the probe 3 at the position of −3 mm is written in the parameter storage region 9d.

Subsequently, the process returns from step 109 to step 102 wherein the gate position is selected as the range being from 0.5 μsec. to 2.5 μsec. and as m=5.

Figure 6:
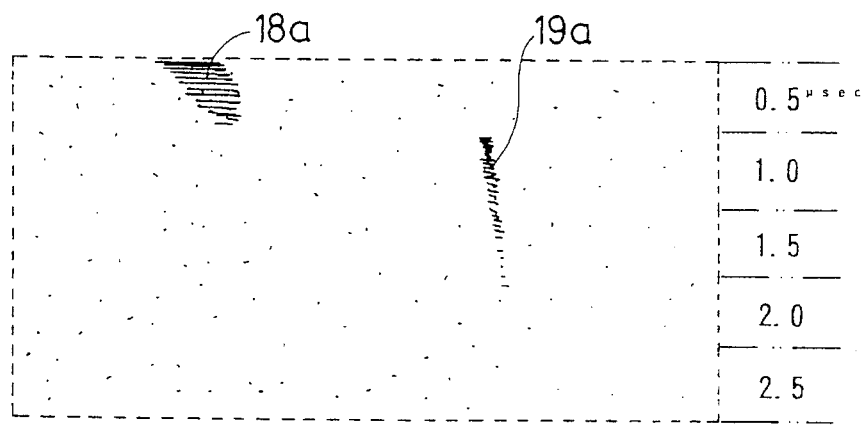
FIG. 6 is a view for explaining measurement images obtained when the gate position is set in 5 steps with respect to the object under examination shown in FIG. 4.

As a result of the above selection, images as illustrated in FIG. 6 are obtained.

In the images ranging from the gate position of 0.5 μsec. to 2.5 μsec., the plating layer 18 in the first step image appears in an image 18a having trailing echo due to echo of the plating layer 18, and in the images of the subsequent steps the images having training echo are disappeared. On the other hand, the image of the wire material 19 appears in the image of the second step in an image 19a of its echo, in the image of the third step the wire material image 19a appears in an image having trailing echo and in the images of the subsequent steps the images having trailing echo disappear.

According to the above measurement images the image of the second step is selected in the same manner as explained above.

With the above operation the second display image is designated, the second parameter 1.0 μsec. stored in the measurement condition table 9e is selected in step 108 and a parameter representing the position of 1.0 μsec. which sets the gate position at the position of 1.0 μsec. is written in the parameter storage region 9d.

Subsequently, the process returns from step 109 to step 102 wherein the gate width is selected as the gate width range being from 1400 n sec. to 600 n sec. and as m=5.

Figure 7:
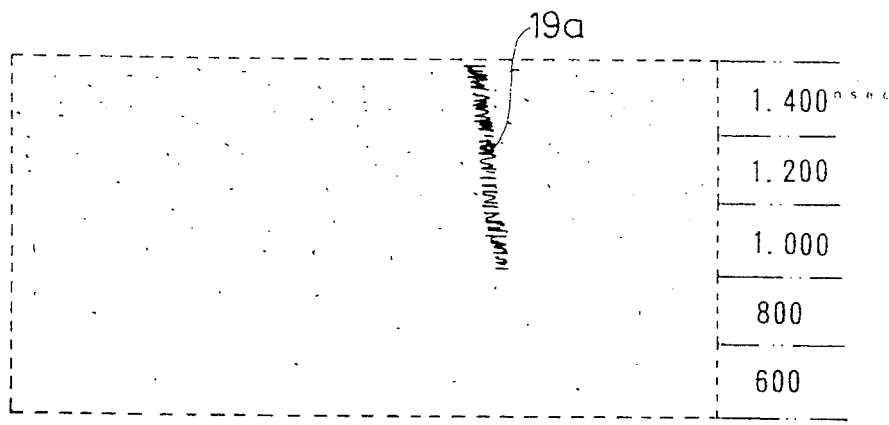
FIG. 7 is a view for explaining measurement images obtained when the gate width is set in 5 steps with respect to the object under examination shown in FIG. 4.

As a result of the above selection, images as illustrated in FIG. 7 are obtained.

In the 5 stepped images ranging from the gate width of 1400 n sec. to 600 n sec., only the echo of the wire material 19 is caught, the wire material 19 in the first step image appears in an image having a wider width, the width of the wire material images in the images of the second step to the subsequent step become close to the actual width thereof, and in the image of the fourth step the image (echo) of the wire material 19 disappears because the gate position displaces from the position of the wire material 19.

According to the above measurement images the image of the third step is selected in the same manner as explained above.

As a result, the third display image is designated, the third parameter 1000 n sec. stored in the measurement condition table 9e is selected in step 108 and a parameter for the gate width which sets the gate width at 1000 n sec. is written in the parameter storage region 9d.

Subsequently, the process returns from step 109 to step 102 wherein the receiver gain is selected as the range being from 15 dB. to 35 dB and as m=5.

Figure 8:
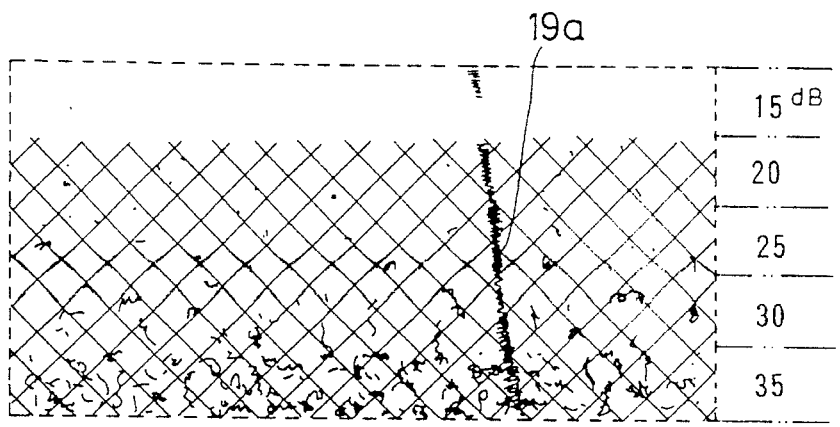
FIG. 8 is a view for explaining measurement images obtained when the probe gain is set in 5 steps with respect to the object under examination shown in FIG. 4.

As a result of the above selection, images as illustrated in FIG. 8 are obtained.

The image of the first step is generally dark and unclear and the images of later steps become bright and clear. However, the images of the fourth and fifth steps contains a lot of noises and in the image of the fifth step the image of the wire material 19 is dominated by noises. According to the above measurement images the image of the third step is selected in the same manner as explained above, and a parameter of gain of 25 dB is written in the parameter storage region 9d.

After determining the respective measurement conditions in the manner as explained above, when the plane scanning operation in step 110 is performed, a desirable C scope measurement image of the object under examination 17 can be obtained. Further, if it is desired to take a cross sectional images thereof, such is obtained by executing at this stage a scanning program which produces a B scope measurement image.

In the above examples the measurement images are sampled out by successively scanning the XY scanning region under 5 stepped measurement conditions. In these examples, since both plating layer 18 and the wire material 19 run substantially parallel with respect to the surface of the object under examination 17, substantially the same images are obtained through the successive scanning operations even when the respective scanning regions for the 5 step are different.

Different from the above production method of the measurement images, a method of obtaining images of m stepped measurement conditions as explained previously wherein the probe is returned to the origin of the XY scanning region after every n lines scanning to scan the same XY scanning region can be applied to the object under examination 17 for its inspection. In such instances, substantially the same images will be obtained for the object under examination 17 as explained above. However, the present method is recomended to apply to an object under examination wherein the internal conditions are different from one scanning region to another scanning region in the range of XY scanning region.

In the above explanation, the m stepped measurement images are displayed at once on the screen, however when the number of m in m steps is large number, the m stepped measurement images can be displayed in 2 or more than 2 screen pictures while allotting a plurality of measurement images less than m for one screen picture, and through switching a plurality of the screen pictures the measurement images are compared and selected.

Industrial Feasibility

As will be apparent from the above explanation, in the present invention the m stepped measurement images corresponding to m pieces of measurement conditions are successively displayed on a screen, the successively displayed images of different measurement conditions are observed and compared and then an optimum image is selected among them, thereby an optimum measurement condition among the m pieces of measurement conditions can be easily set.

As a result, even a person inexperienced in ultrasonic measurement can easily set an optimum condition or a close to optimum proper measurement condition in comparatively short time.

We claim:

1. An ultrasonic inspection and imaging instrument, comprising:

means for dividing a scanning range of an object under examination into m pieces (m is an integer equal to or more than 2) in a subscanning direction;

means for setting one of measurement conditions or one of measurement parameters in each of m steps;

means for performing an ultrasonic measurement on the object under examination while allotting successively the m-stepped measurement conditions or the m-stepped measurement parameters to the respective scanning regions divided in the subscanning direction;

display means for displaying a plurality of measurement images obtained under the m-stepped measurement conditions on a display screen so as to permit comparison of the measurement images on the display screen; and means for setting one of the m-stepped measurement conditions or one of the m-stepped parameters which corresponds to an image selected from the displayed screen as the measurement condition or measurement parameter for the object under examination.

2. An ultrasonic inspection and imaging instrument according to claim 1, wherein the m-stepped scans are set over the same plane scanning range, and wherein every successive allotment of the m-stepped measurement conditions or m-stepped parameters is repeated over the same plane scanning range to perform m measurements.

3. An ultrasonic inspection and imaging instrument according to claim 1, wherein the plurality of the measurement images are formed as one display screen picture, the horizontal scanning lines on the display screen correspond to the main scanning lines during the measurement, and each of the measurement images is displayed on a respective scanning region as an image of horizontal scanning lines of a number corresponding to an integer portion of a quotient determined by dividing the total horizontal scanning line number in the display range for one screen picture by m.

4. An ultrasonic inspection and imaging instrument according to claim 2, wherein the plurality of the measurement images are formed as one display screen picture, the horizontal scanning lines on the display screen correspond to the main scanning lines during the measurement, and each of the measurement images is displayed on a respective scanning region as an image of horizontal scanning lines of a number corresponding to an integer portion of a quotient determined by dividing the total horizontal scanning line number in the display range for one screen picture by m.

5. An ultrasonic inspection and imaging instrument according to claim 3, further comprising a processor, a memory, and an input unit, wherein the number of m and the range of the measurement condition or the range of the measurement parameter are inputted via said input unit and further comprising means for producing the m-stepped measurement conditions or m-stepped measurement parameters with regard to the inputted range of the measurement condition or the inputted range of the measurement parameter according to the number of m and for storing the same in said memory, wherein the m-stepped measurement conditions or the m-stepped measurement parameters are successively read out from said memory and set.

6. An ultrasonic inspection and imaging instrument according to claim 4, further comprising a processor, a memory, and an input unit, wherein the number of m and the range of the measurement condition or the range of the measurement parameter are inputted via said input unit and further comprising means for producing the m-stepped measurement conditions or m-stepped measurement parameters with regard to the inputted range of the measurement condition or the inputted range of the measurement parameter according to the number of m and for storing the same in said memory, wherein the m-stepped measurement conditions or the m-stepped measurement parameters are successively read out from said memory and set.

7. An ultrasonic inspection and imaging instrument according to claim 6, wherein the image selection is performed via said input unit by designating one of the measurement images displayed on the display screen picture, through reading in the vertical address of the designated image position on the screen picture, the order of the display region of the measurement image on the display screen picture being determined and the measurement condition or the measurement parameter being selected according to the determined order.

8. An ultrasonic inspection and imaging instrument according to claim 6, wherein the range of the measurement condition or the range of the measurement parameter is defined by a reference position and number of pitches from the reference position.

9. An ultrasonic inspection and imaging instrument according to claim 7, further comprising means for calculating a scanning line number corresponding to an integer portion of 1/m of the total horizontal scanning line number on the display screen picture according to the number of m, and for allotting the same for the respective scanning regions.

10. An ultrasonic inspection and imaging instrument according to claim 6, wherein the m-stepped measurement conditions or the m-stepped measurement parameters are set successively according to the order stored in said memory as the respective measurement conditions or measurement parameters and the respective measurements being performed thereunder, the measurement images and the corresponding measurement conditions or measurement parameters being successively displayed on the screen according to the order, the displayed measurement condition or measurement parameter being inputted via said input unit, and one of the m-stepped measurement conditions or one of the m-stepped parameters corresponding to the selected measurement image being selected.

* * * * *